United States Patent [19]

Michalos

[11] Patent Number: 5,522,829
[45] Date of Patent: Jun. 4, 1996

[54] SURGICAL CUTTING INSTRUMENT

[75] Inventor: Peter Michalos, New York, N.Y.

[73] Assignee: Arthur D. Little Enterprises, Inc., Cambridge, Mass.

[21] Appl. No.: 303,399

[22] Filed: Sep. 9, 1994

Related U.S. Application Data

[63] Continuation-in-part of Ser. No. 162,807, Dec. 3, 1993, abandoned, which is a continuation of Ser. No. 871,265, Apr. 16, 1992, abandoned.

[51] Int. Cl.⁶ .................................................. A61B 17/32
[52] U.S. Cl. .......................... 606/170; 606/167; 606/107; 433/102
[58] Field of Search ..................................... 606/107, 170, 606/167, 166; 433/102, 103, 105, 144, 112

[56] References Cited

U.S. PATENT DOCUMENTS

| | | |
|---|---|---|
| 873,100 | 12/1907 | Skalstad ................................... 433/102 |
| 2,469,261 | 5/1949 | Cooper ..................................... 433/112 |
| 3,471,929 | 10/1969 | Boone ...................................... 433/144 |
| 3,740,853 | 6/1973 | Brahler . |
| 3,906,636 | 9/1975 | Rainey et al. . |
| 4,002,169 | 1/1977 | Cupier, II . |
| 4,071,029 | 1/1978 | Richmond et al. . |
| 4,278,429 | 7/1981 | Straihammer et al. ................. 433/105 |
| 4,708,138 | 11/1987 | Pazandak ............................... 606/107 |
| 4,773,415 | 9/1988 | Tan . |
| 4,955,894 | 9/1990 | Herman . |
| 5,062,796 | 11/1991 | Rosenberg .............................. 433/103 |
| 5,133,727 | 7/1992 | Bales et al. . |
| 5,133,735 | 7/1992 | Slater et al. . |
| 5,261,923 | 11/1993 | Soares .................................... 606/170 |
| 5,292,330 | 5/1994 | Shutt ...................................... 606/170 |

Primary Examiner—Corrine M. McDermott
Assistant Examiner—N. Kent Gring
Attorney, Agent, or Firm—Weingarten, Schurgin, Gagnebin & Hayes

[57] ABSTRACT

The invention relates to a remotely operable surgical cutting instrument, useful, for instance, in microsurgical procedures, having a two portion main body with one portion oriented at an angle with respect to the other, and a blade having an arcuate cutting edge mounted at one end of the body.

32 Claims, 8 Drawing Sheets

SURGICAL CUTTING INSTRUMENT

RELATED APPLICATIONS

This application is a continuation-in-part application of U.S. Ser. No. 08/162,807, filed Dec. 3, 1993, now abandoned, which in turn is a continuation application of U.S. Ser. No. 07/871,265, filed Apr. 16, 1992, now abandoned.

FIELD OF THE INVENTION

The present invention relates to surgical cutting instruments, especially small scale, remotely operable surgical knives or scissors, useful for performing microsurgical procedures.

BACKGROUND OF THE INVENTION

A common procedure in ophthalmology to remove cataracts is to use phacoemulcification and suction to remove the affected lens from the eye. This procedure is shown and described, for instance, in Cupler, U.S. Pat. No. 4,002,169, in which access to the lens is achieved through the sclera or limbus, then through the opening in the iris, and finally through the anterior capsular membrane. Although, as shown in Cupler, it may be possible to gain access to the lens and remove it by piercing the anterior capsular membrane, it is more common to remove a circular piece of the membrane by a "capsulotomy" procedure, for example by tearing out a portion of the membrane with a needle and forceps. Alternatively, it is known to free the desired membrane portion with a surgical knife. In this type of procedure, it is essential to maintain the cutting edge of the knife so that it is oriented in the proper direction during the entire circular cut. This may be difficult if the cutting instrument is introduced through the single incision in the sclera that is used for the other steps in the cataract removal.

One example of a surgical knife appropriate for a capsulotomy is disclosed in Pazandak, U.S. Pat. No. 4,708,138, in which a knife blade is attached to an extension handle at a swivel point, the cutting portion of the blade being off center from the swivel point. The knife is directed by sideways motion of the end of the handle removed from the blade attachment point, and the shape and method of attachment of the cutting blade to the handle cause the blade to orient itself with the cutting edge forward, in the direction of movement of the blade, as long as movement of the blade is continuous.

SUMMARY OF THE INVENTION

The invention features a surgical knife useful in microsurgical procedures that includes a two portion main body with one portion oriented at an angle with respect to the other portion, and a blade having an arcuate cutting edge, the blade being mounted at one end of the body and the orientation of the blade with respect to the body being alterable during cutting.

As used herein, "arcuate" refers to a curved shape as in a semi-circular or circular shape. Thus, in preferred embodiments, the arcuate blade is a cutting edge of semi-circular or circular shape. "Semi-circular" refers to a cutting edge that does not form a complete circle, i.e., is less than 360 degrees, preferably less than 240 degrees, most preferably is about 180 degrees.

The surgical knife is especially useful in tissue cutting procedures in which a desired cutting path is chosen by the surgeon. For example, the cutting path may be of a circular or semi-circular shape, as in capsulotomy procedures where a circular piece of ocular tissue is cut and removed, or the cutting path may be straight or angled, e.g., as in arthroscopic or laparoscopic applications. The blade is thus applied to the tissue along a desired cutting path, and is useful for implementing various types of cuts, e.g., for cutting through the tissue, for intermittent cutting, or for scoring of the tissue, depending upon the amount of pressure applied to the tissue through the cutting edge. The blade also may be configured so as to more easily accomplish a particular type of tissue cut; for example, for scoring or intermittent cutting. As used herein, "scoring" refers to cutting into a tissue layer without cutting through the layer. Alternatively, the blade may be configured so as to allow for intermittent cutting through the tissue. "Intermittent" cutting refers to implementing discrete cuts through the layer of tissue to be cut, while leaving uncut tissue in between the discrete cuts.

In other preferred embodiments, the cutting edge is of a sharpness sufficient to cut into a tissue layer without cutting through the tissue layer. As used herein, "sufficient sharpness" refers to a degree of sharpness that allows for easy and clean piercing of the tissue, without tearing, upon application of an amount of pressure of the cutting edge against the tissue that is comfortable to the user of the knife. Of course, the amount of pressure that is needed to accomplish a given type of cut is determined by the skilled user, as described further below.

In yet other preferred embodiments, the cutting edge is either continuous or serrated. As used herein, "serrated" refers to the conventional meaning of this term, e.g., the edge is notched or toothed, the notches or teeth being pointed, flat, or curved at their outer edge so as to deliver intermittent discrete cuts of a desired length.

In yet other preferred embodiments, the surgical knife further comprises a linear rotatable element, i.e., a turning unit, disposed within the main instrument body. The blade is mounted on the turning unit at one end of the main instrument body and is disposed at an angle to the primary instrument body axis. The orientation of the cutting edge of the blade with respect to the main body is determined by movement of the turning unit at the end distal to the blade mounting end.

In another aspect, the surgical knife includes a turning unit comprising either a flexible element having greater flexibility than the main body or a band, the flexible element or band being aligned along the primary axis within the main body and cooperating with a blade mount at one end and a knob at the other end of the main body so as to allow alteration of the orientation of the blade with respect to the main body.

Preferably, the knife includes a blade mount and a knob; and the band is wrapped around the blade mount at one end and the knob at the other end of the main body.

The invention also features a remotely operable surgical knife that includes a tubular main body having a primary axis and a turning unit disposed within the main instrument body. A blade is mounted on the turning unit at one end of the main instrument body and is disposed at an angle to the primary instrument body axis. The orientation of the cutting edge of the blade with respect to the main body is determined by movement of the turning unit at the end distal to the blade mounting end.

Preferred embodiments of the surgical knife include a tubular main body which is an elongated first portion, open at one end, and a shorter second portion, open at one end and extending from the first portion distal to the open end of the first portion to form an angle greater than 45° to the first portion. The turning unit of the knife includes a turning mechanism in the main body at the juncture of the first and second portions; a linear rotatable element disposed through the main body, e.g., a movable rod or wire or other connecting element through the first portion of the main body, which has one end attached to the turning mechanism; and a blade mounting portion in the second portion of the main body and attached to the turning mechanism. The blade is mounted on the blade mounting portion of the turning unit, and movement of the other end of the moveable element causes rotation of the blade about an axis generally aligned with the second portion of the main body. The blade may be discarded and replaced with a fresh blade for each use. Alternatively, the entire surgical knife may be discarded after use.

Preferably, the angle between the first and second portions of the main body of the knife is between 80° and 110°, and the knife blade is of a circular configuration. The turning mechanism of the turning unit is preferably a micro gear unit, for example, transversely oriented bevel gears or a rack and pinion unit. Alternatively, the turning mechanism includes a flexible element, such as a silicone rubber, a polyurethane elastomer, or a coiled spring, that has greater flexibility than the movable element portion of the unit. Or the entire turning unit could comprise a rotatable element disposed through the body of the knife.

In another embodiment, the body of the instrument and micro gear turning mechanism have similar configurations to those of the surgical knife described above, but the knife blade is replaced by micro dimension scissors, one handle of which is attached directly to the end of the turning unit. Orientation of the scissors is maintained along the desired cutting path by rotation of the micro gear turning mechanism, and the scissors are operated to make the desired cut by movement of an additional wire extending from the scissors through the main body of the instrument. Preferably, the turning unit and the scissors control wire are operated by manual control elements in the shape of scissors handles, and portions of the turning unit and the main instrument body are flexible.

Because of the small size of the cutting instrument and because movement of the cutting portion is precisely directed from a remote position, a remotely operable surgical cutting instrument according to the invention is easy to use in small incision surgery, where quick entry to and exit from the site of the operation is required. The cutting portion of the instrument can be directed along the cutting pattern desired at all times during the surgical procedure, whether cutting is made in a continuous process or discontinuously. In the circular or semicircular configuration the knife blade of the surgical knife is readily reversible. The particular advantages of a circular blade are that the knife edge covers a larger surface of the eye and therefore can give better depth control. The cutting instrument is simple and rugged in design. Therefore, numerous embodiments can be inexpensively manufactured from readily available materials and then discarded without incurring any great expense.

The invention also encompasses methods of performing microsurgery using embodiments of the surgical knife described herein.

Thus, in one method, the arcuate cutting edge is applied to a tissue layer and moved along a chosen cutting path. The pressure applied to the tissue layer is sufficient to cut through the layer of tissue without tearing or otherwise damaging the tissue.

In another method, known as "scoring", a surgical knife in which the blade comprises an arcuate or pointed cutting edge, as described herein, is used. The scoring method includes applying the arcuate cutting edge to a tissue layer with pressure of the cutting edge against the tissue layer sufficient to cut into the tissue layer in a continuous manner, but insufficient to cut through the tissue layer. Once the tissue is scored, the tissue layer is then peeled or pulled off. In this scoring method, a conventional sharp cutting edge may be used provided the pressure applied to the cutting edge against the tissue layer is less than the pressure that is applied to the same tissue using the same cutting edge sharpness when making a cut completely through the tissue layer. The amount of pressure necessary to perform the procedure will, of course, be judged by one of skill in the art during the surgical procedure, e.g., the surgeon performing the procedure.

Alternatively, the scoring method may employ a cutting edge that is less sharp than a conventional edge such that the pressure applied to the cutting edge against the tissue layer need not be less than the normal amount of pressure using a sharp edge, and may in fact be increased. Again, the amount of pressure necessary to achieve scoring of the tissue layer will be determined by the skilled surgeon during the procedure. The pressure will vary according to the type of tissue to be cut, the thickness of the tissue layer, and the relative sharpness of the cutting edge.

In preferred embodiments of this method of the invention, cutting may be in a continuous manner or may be intermittent.

Another method of the invention employs a surgical knife having a serrated cutting edge. This method, known as "intermittent" cutting, involves applying the serrated cutting edge to the tissue layer in a continuous manner using an amount of pressure sufficient to achieve intermittent cuts through the tissue. When a serrated cutting edge is used, pressure will be applied continuously, with the serrations in the cutting edge accomplishing the desired dis-continuous cutting pattern. Thereafter, the cut tissue is peeled or pulled off.

An alternative method of intermittent cutting is achieved using a non-serrated blade, i.e., a blade of continuous sharpness along its arcuate cutting edge. According to this method, the blade is applied to the tissue layer in a discontinuous manner. That is, the cutting edge cuts into the tissue upon application of pressure on the blade against the tissue layer, pressure is then released for a chosen distance along the cutting path, and then alternately reapplied and released. The cut tissue is then peeled or pulled off.

The invention will be more fully understood with reference to the detailed description, the accompanying drawings, and the claims.

BRIEF DESCRIPTION OF THE DRAWINGS

The drawings are first briefly described.

DESCRIPTION OF PREFERRED EMBODIMENTS

A surgical knife for micro surgery must be sized at its cutting end so as to permit insertion into the micro scale surgical field of the target tissue and yet be large enough at its opposite end to be held comfortably in the hand of the operating surgeon. Preferably, the knife is configured so that it may be introduced through the single incision into the portion of the body containing the target tissue. For example, a surgical knife for capsulotomy must be sized at its cutting end so as to permit insertion into the relatively small field of the eye. The knife will be configured so as to be introduced via a single incision into the sclera that is used for other steps in cataract removal.

The description provided below of the surgical knife of the invention and methods of use therefore is made with respect to a capsulotomy knife and procedure. It will be understood that the surgical knife is not intended solely for capsulotomy procedures, but may be used in other types of surgical procedures that require entry into the surgical site with a minimum of intrusion, cutting of a tissue at a target site, and manipulation of the cutting blade at the cutting site via a mechanism which places the surgeon's hand at a distance from the target site. It will be readily apparent to one of skill in the art that the knife may be used in procedures other than capsulotomy and how to perform such procedures using a surgical knife of the invention.

Figure 1:
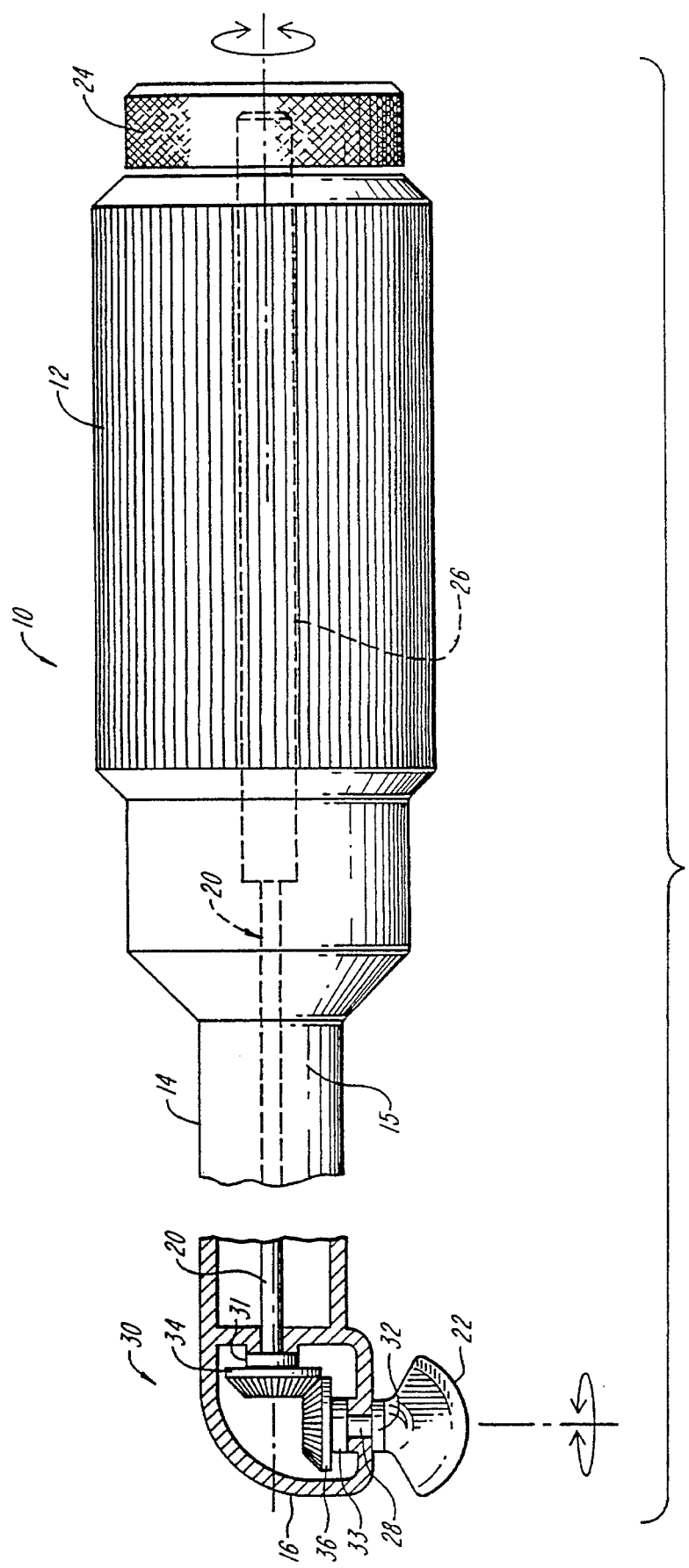
FIG. 1 is a side perspective view of a surgical knife according to the invention.

Referring first to FIG. 1, a capsulotomy knife 10 has a 15 cm long tubular main body 12 of either plastic or stainless steel, which is open at each end and includes an elongated first portion 14 and a relatively short second portion 16. The elongated portion of the knife includes a handle 15 of approximately 7 mm in diameter and steps down to a diameter of less than 1 mm at the junction with the second portion. The second portion of the knife extends at a substantial angle to the first portion; in preferred embodiments of the invention, this angle is 80°–110° (preferably 90°).

Figure 2:
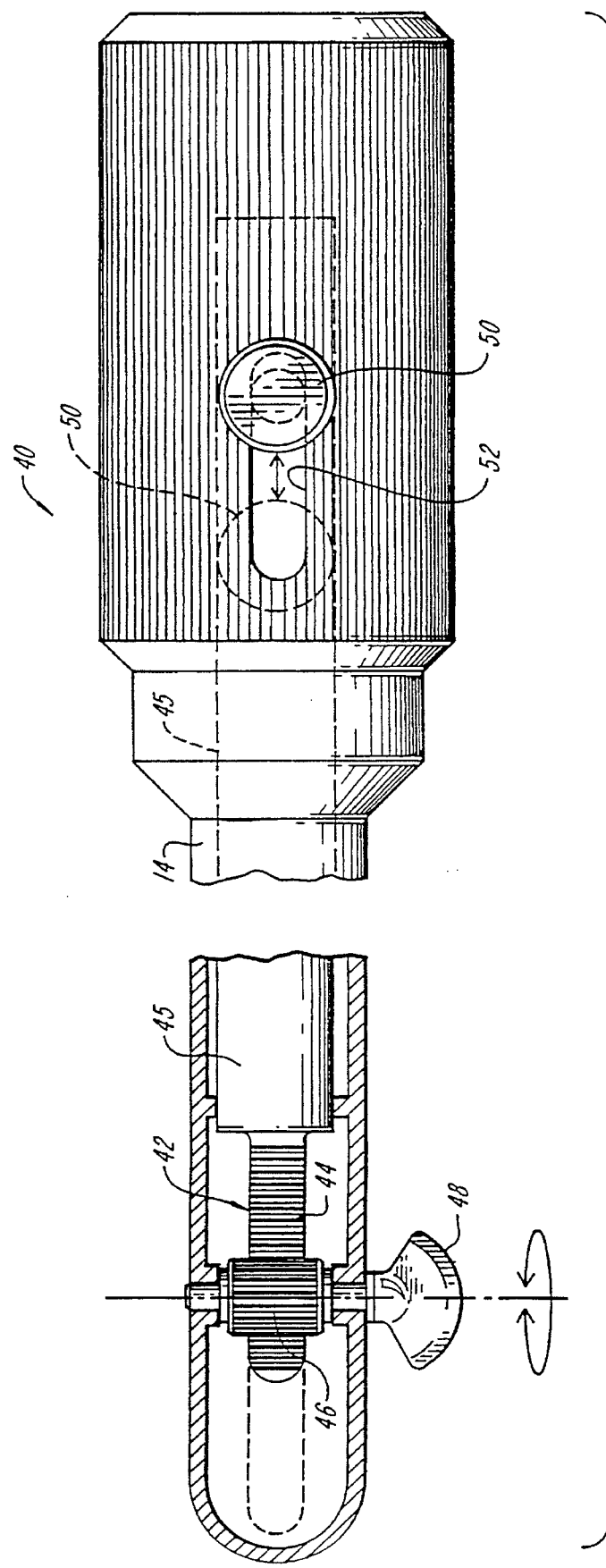
FIG. 2 is a side perspective view of another embodiment of a surgical knife according to the invention.
Figure 3:
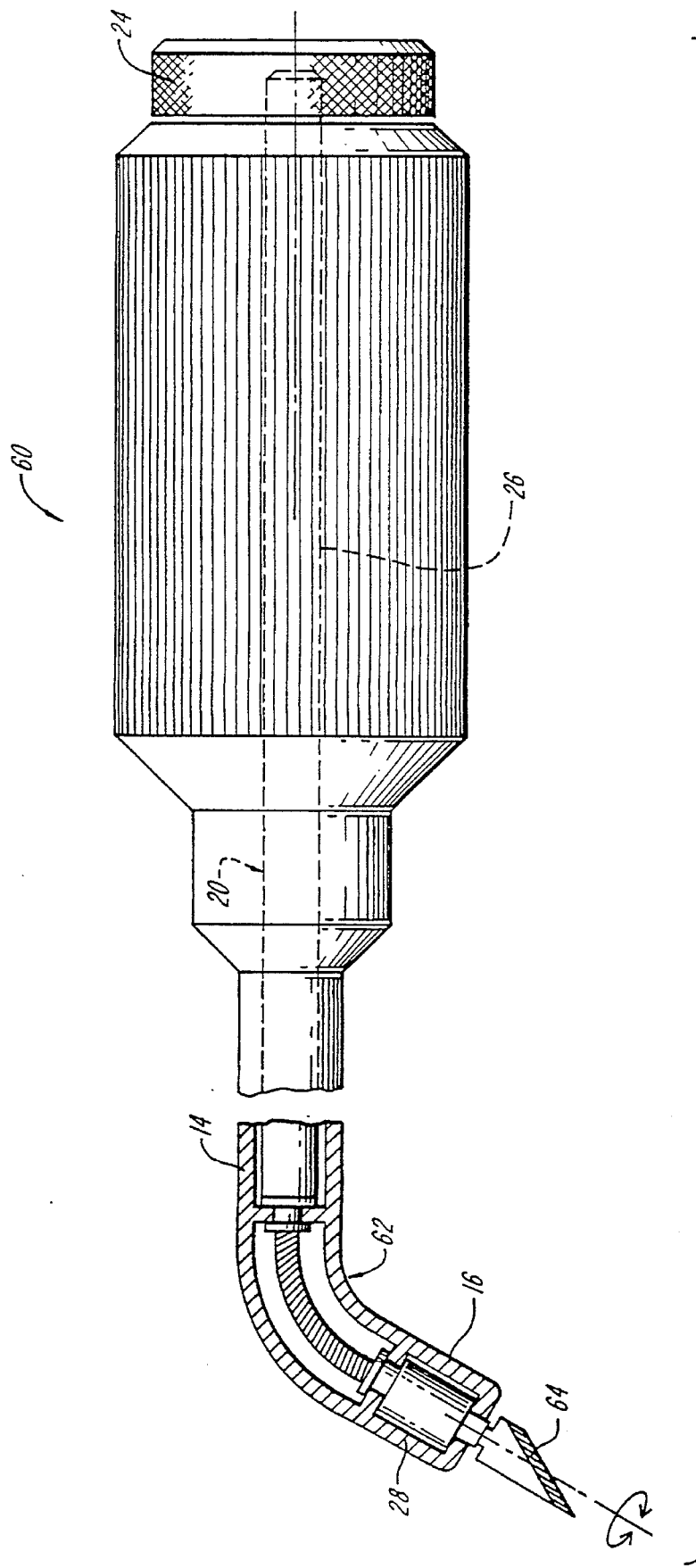
FIG. 3 is a side perspective view of another embodiment of a surgical knife according to the invention.

A turning unit 20 extends through the main body of the knife, having a blade 22 mounted thereon at the open end of the second portion of the body and a control knob 24 at the open end of the first portion. Knife blade 22 is attached by any convenient means, and blade mounting portion 28 is journalled for rotation, as shown, or in any other convenient manner to suit the particular implementation. The turning unit itself comprises three sections: first, a movable polytetrafluoroethylene (e.g., Teflon®) or stainless steel rod 26 through the first portion 14 of the main body, which attaches to the control knob; second, a blade mounting portion 28 through the second portion 16 of the main knife body, to which knife blade 22 is attached; and, third, a micro gear turning mechanism 30 at the juncture of the first and second portions, which connects the movable wire with the blade mounting portion of the unit. As shown in FIG. 1, knife blade 22 is circular and is suspended from blade mount 32. However, numerous other blade configurations, such as semi-circular or triangular as shown in FIGS. 2 and 3, are suitable depending on the application. Micro gear mechanism 30 has two edge engaging bevel gears 34, 36 oriented at right angles and supported by bushings 31, 33. Rotation of control knob 24 by a surgeon, and consequent rotation of rod 26 and bevel gear 34, is translated into rotation of bevel gear 36 and knife blade mount pin 32 and, thus, positive controlled rotation of the knife blade itself a full 360°. A typical micro gear, which can be stainless steel or plastic, is about 0.5 mm in diameter, the dimensions of a gear in a small analog watch, and can be machined to have bevelled edges at any desired angle.

In an alternate configuration 40, shown in FIG. 2, micro gear mechanism 42 comprises a rack gear 44 mounted on the end of movable rod 45 and engaging the teeth of a pinion gear 46, to which knife blade 48 is attached. Slide control knob 50 is connected to rod 45 through a slide opening 52 in main knife body portion 14. As the slide control knob is moved by a surgeon within slide opening 52, passage of the rack gear 44 past the side of pinion gear 46 causes rotation of the gear and, thus, rotation of the knife blade 48. In this FIG. 2 embodiment, part of the main knife body portion 14 extends past the micro gear mechanism to accommodate the movement of rack gear 44.

Figure 9:
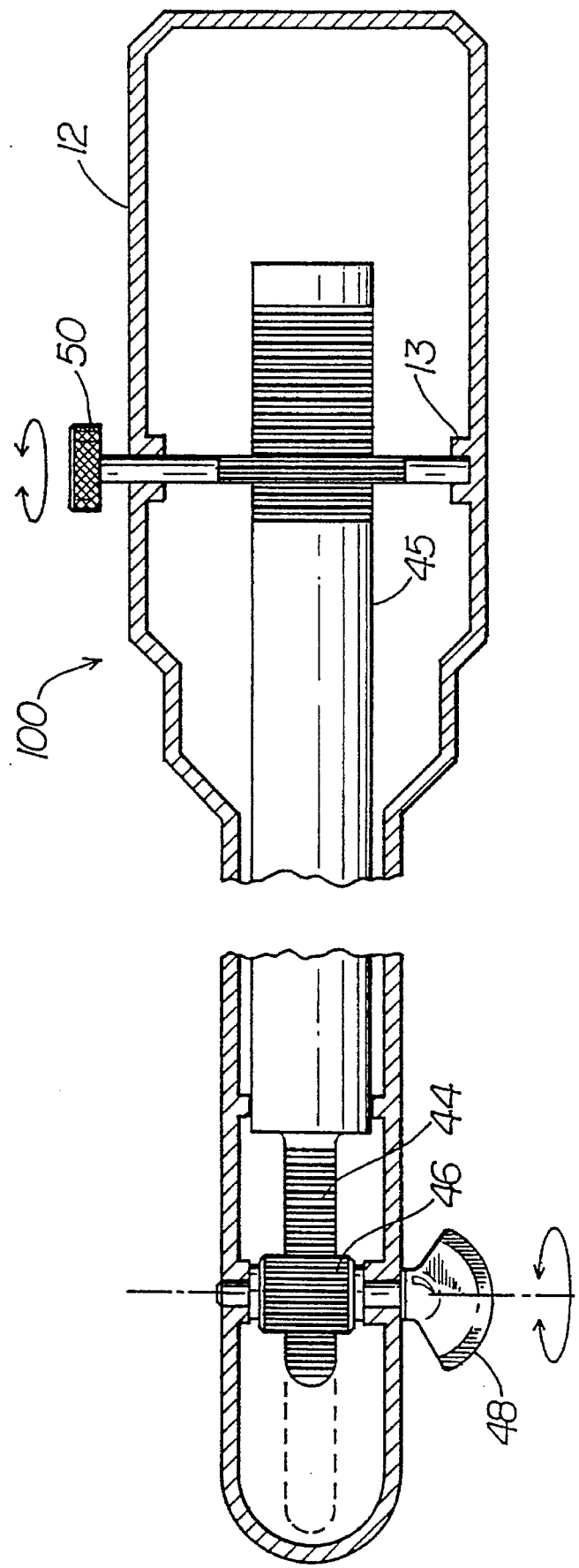
FIG. 9 is a side perspective view of another embodiment of the turning mechanism of a surgical knife of the invention.

In an alternative embodiment 100 of the rack gear mechanism, shown in FIG. 9, slide control knob 50 operates movement of rack gear 44 past the side of pinion gear 46 via turning of knob 50. In order to minimize any sideways motion of knob 50 during use, knob 50 may be attached at its distal end to main body 12 via adaptor 13. Knob 50 is journalled where it contacts movable rod 45, which is also journalled. Knob 50 thus cooperates with rod 45 such that turning of knob 50 in either direction results in movement of rod 45. Movement of rod 45 translates into turning of blade 48 via cooperation between the journalled portions of rack gear 44 and pinion gear 46, as described above. Slide control knob 50 may turn up to 360 degrees or more, in either direction, until blade 48 is correspondingly turned to the desired degree. Optimally, control knob 50 is turned until blade 48 is correspondingly turned to approximately a 60 degree angle in either direction. In the various embodiments of the invention, the entire instrument is on the order of 90–160 mm in length, optimally approximately 120–130 mm in length, the shaft diameter at the leading (i.e., blade-attachment) end of the shaft is on the order of 1–4 mm and optimally 2–3 mm in diameter, and the blade is on the order of 1–3 mm in width and 0.5–2 mm in height, optimally 1.5 mm width and 1 mm height. The instrument is generally of a size which allows for holding of the handle in the palm of the hand. For those embodiments including a knob in the handle portion of the instrument, the knob may be operated with the thumb or index finger of the same hand that holds the instrument.

Figure 10:
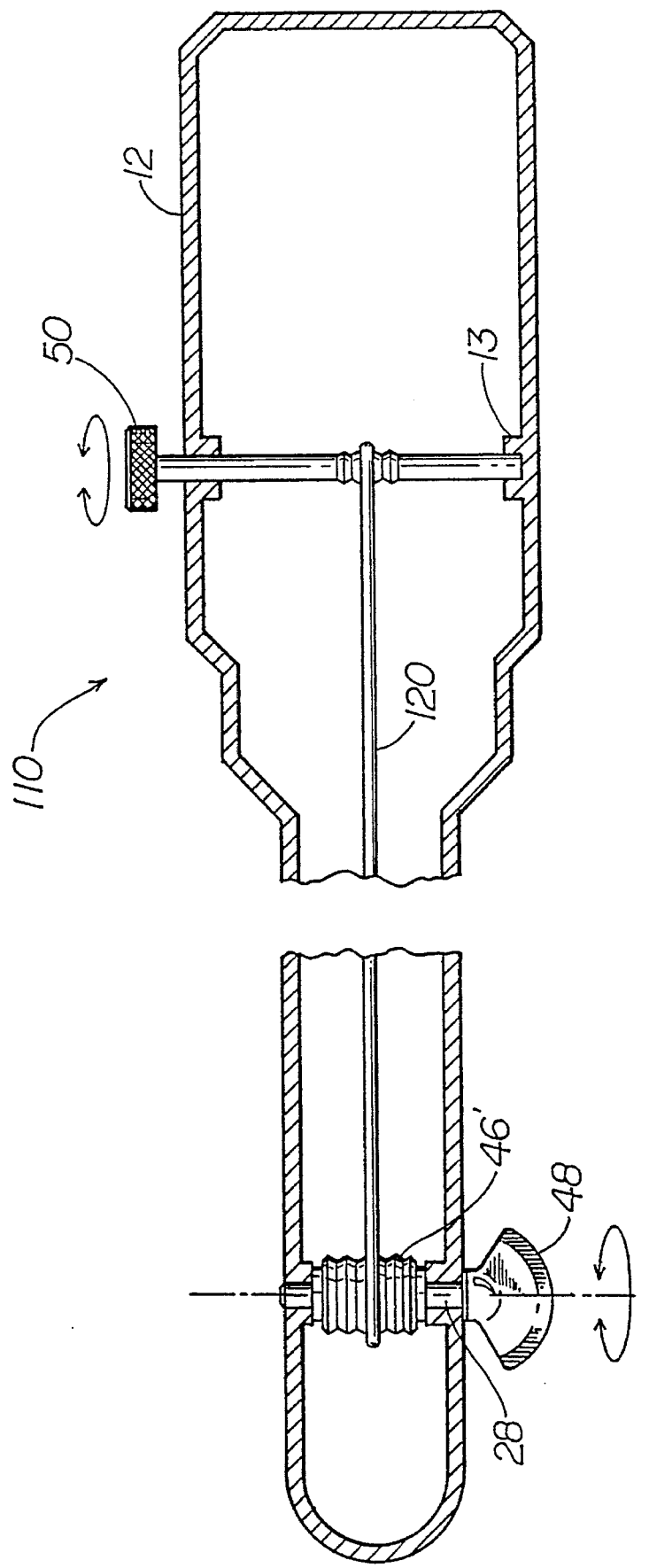
FIG. 10 is a side perspective view of yet another embodiment of the turning mechanism of a surgical knife of the invention.

In a fourth embodiment 110 of the capsulotomy knife, shown in FIG. 10, the turning mechanism comprises a turning knob 50 and a band 120 extending around or attached to the turning knob 50 at one end and extending through the handle 12 of the instrument and wound around the blade pinion gear 46' at the other end. In this embodiment, pinion gear 46' is journalled horizontally for rotation such that band 120 may catch in a crevice of the journalled portion of gear 46'. Knob 50 is also horizontally journalled such that band 120 wraps around knob 50 and may catch in a crevice of the journalled portion of knob 50. Turning of the blade 48 is accomplished by turning of knob 50; tension in band 120 is sufficient to create friction between the band and the journalled gear 46', thus causing mounting portion 28 and attached blade 48 to turn in a desired direction and to a desired degree. The band may be made of any material in which tension may be induced sufficient to cause frictional movement of the journalled blade mounting portion 28. For example, the band may be made of an elastomeric material such as a rubber, or a non-elastomeric material such as a flexible plastic or metal.

In a fifth embodiment 60 of the capsulotomy knife, shown in FIG. 3, the turning mechanism 62 of the turning unit is simply an element that is more flexible than the main portion of the unit so that turning unit 20 can accommodate to the shape of the main knife body 12 without kinking. A suitable element to provide this function is a coiled wire spring which is attached at respective ends of moveable rod 26 and the blade mounting portion 28. A flexible material such as a length of silicone rubber, Teflon®, or polyurethane elastomer would also serve the same purpose. The flexible nature of the turning mechanism of embodiment 60 allows rotation of knob 24 to result directly in rotation of the surgical knife blade 64.

Figure 7:
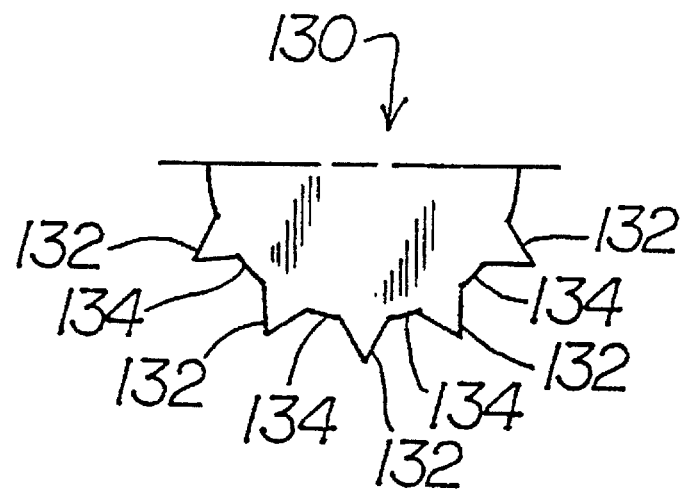
FIG. 7 is a side perspective view of an embodiment of the arcuate cutting edge shown in FIG. 1, in which the cutting edge is serrated.
Figure 8:
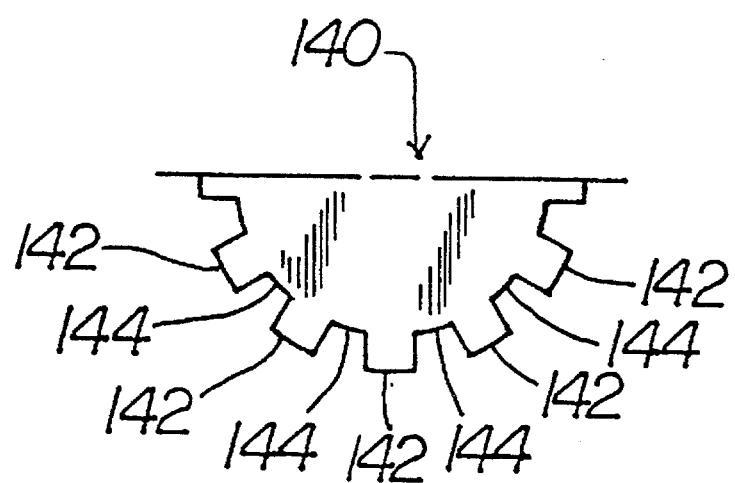
FIG. 8 is a side perspective view of another embodiment of the arcuate cutting edge shown in FIG. 1, in which the cutting edge is also serrated.

The cutting edge of the blade portion of a surgical knife according to the invention is, as described herein, of an arcuate or triangular (diamond) shape, with an arcuate shape being a semi-circular or circular shape. A cutting edge useful in the invention may be an extremely sharp, fine edge or may be slightly less sharp or relatively dull, as the procedure requires. As described above, less sharp or relatively dull edges are especially useful in scoring types of cutting methods. In addition, a cutting edge useful in the invention will typically be a continuous edge with no serrations. Alternatively, the cutting edge may be serrated, as shown in FIGS. 7 and 8. FIG. 7 shows a serrated cutting edge 130 in which the teeth 132 are triangular or diamond shaped and interrupted by recessed areas 132 that do not make cutting contact with the tissue. FIG. 8 shows a serrated cutting edge 140 in which the teeth 142 present an arcuate cutting edge and are interrupted by recessed portions 144 that do not make cutting contact with the tissue. Thus, the serrated cutting edges allow for implementation of discontinuous or intermittent cuts along the target cutting line.

Figure 4:
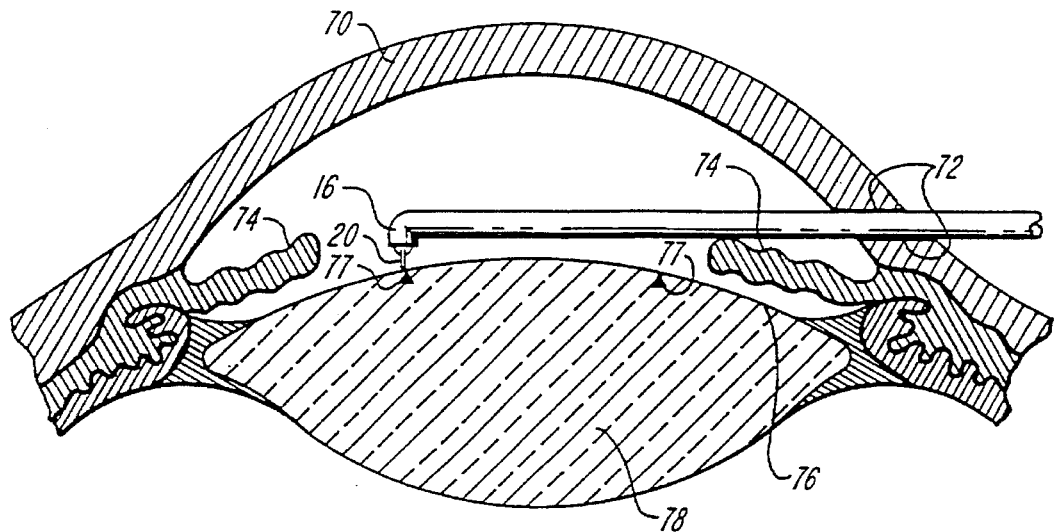
FIG. 4 is an axial sectional view of a human eye, showing the invention in use.
Figure 5:
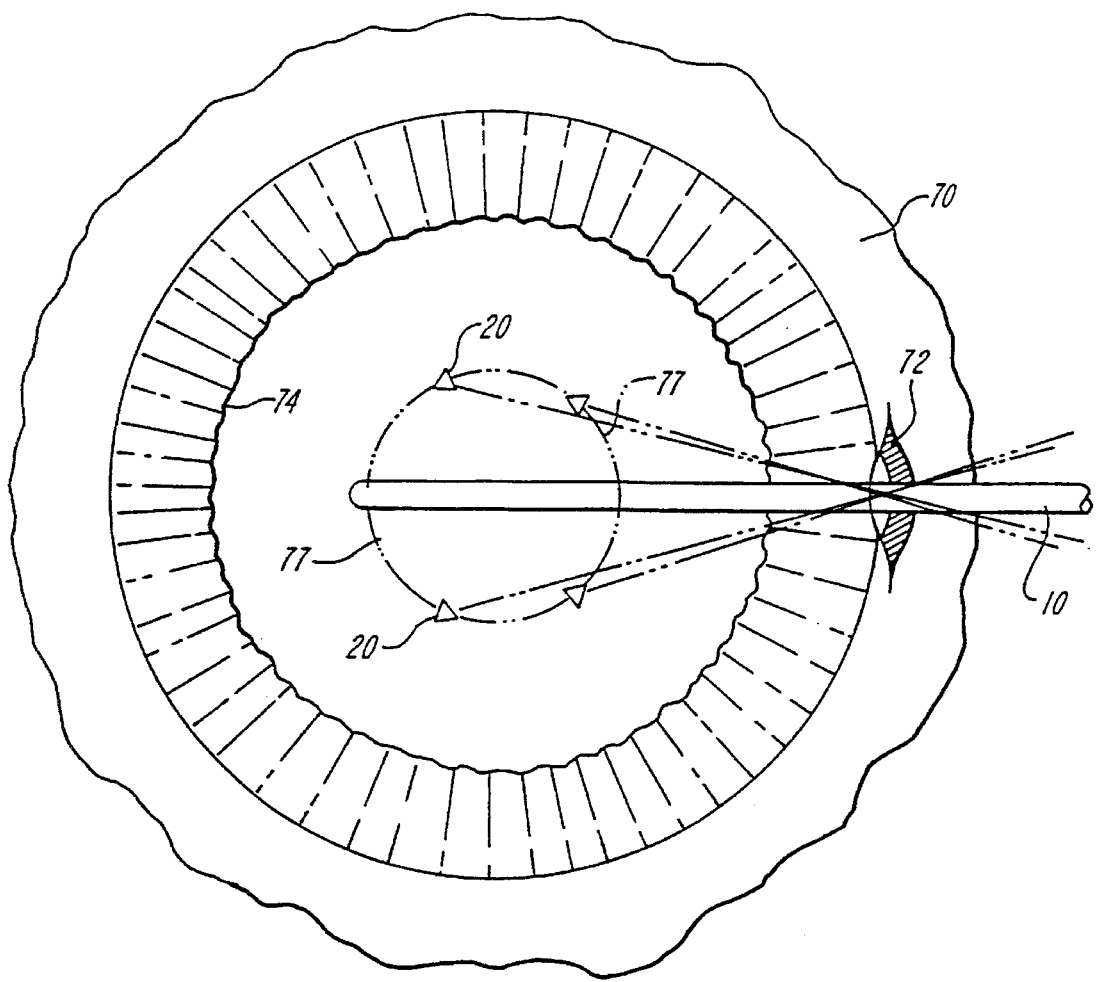
FIG. 5 is a transverse sectional view of the eye, showing the path taken by a capsulotomy knife according to the invention during use.

The operation and the advantages of the present invention will now be readily understood in view of the above description. FIGS. 4 and 5 demonstrate the manner in which a capsulotomy knife is used in the capsulotomy procedure on a human eye 70. An incision 72 is made through the sclera and conjunctiva, the cornea is lifted, and the knife 10 is inserted into the eye. The second portion 16 of knife 10 is then passed through the dilated iris 74 and turned so that it is oriented axially of the eye and is positioned above and at a right angle to the general plane of the anterior capsular membrane 76, which overlies the lens 78, the portion of the eye eventually to be removed.

At this point in the procedure, the knife is lowered and the blade 22 is moved along a circular path 77 defining the section of the anterior capsular membrane to be removed. As shown in FIG. 5, the orientation of the knife blade along the circular path is maintained by rotation of the turning knob 24. This movement serves to rotate blade 22 with respect to the main body of the knife, as described above. The aspect of the blade and its maintenance on the selected path can be facilitated through microscopic observation, as is customary in such surgical procedures.

Additional operations and advantages of the present invention are found in the uses of the various cutting edges disclosed herein. The continuous arcuate cutting edge (as pictured in FIG. 1) may be used to make a continuous cut through a tissue layer, a dis-continuous (i.e., intermittent) cut through the layer, or a scored type of cut into but not completely through the tissue layer. These three types of cutting are accomplished using a single blade configuration by varying the pressure applied to the instrument during cutting and by varying the length of tissue cut along the cutting path. For example, a continuous cut through the tissue layer is achieved by applying enough continuous pressure through the blade cutting edge against the tissue layer to allow the cutting edge to slice through the tissue layer. This amount of pressure is then maintained as the blade is guided along the chosen cutting path. As explained above, one of skill in the art, having practiced the selected type of surgery many times, and being familiar with the relative strength of the target tissue and blade sharpness, will easily determine what amount of pressure is needed to accomplish the task.

Alternatively, where dis-continuous cutting of a tissue layer is desired using the continuous cutting edge, the pressure manually applied to the instrument by the hand of the surgeon, is varied for a time sufficient to implement discrete cuts through the tissue layer along the chosen cutting path. Thus, when pressure is applied to the instrument, the cutting edge cuts through the tissue layer for a first given distance along the cutting path. This is followed by releasing the applied pressure enough to disengage the sharp cutting edge from the tissue surface for a second given distance. Thereafter, pressure is reapplied and released as many times as is necessary to complete the cutting path. The uncut portions of tissue between the cut portions serve to help maintain an intact tissue layer and thus to prevent tearing prior to removal of the cut layer of tissue. At the same time, implementation of discrete intermittent cuts in this way allows for easy removal of the cut tissue by simply lifting the cut tissue layer and pulling the cut tissue away from its actual position. The uncut intermittent portions of tissue will neatly tear between the cut portions to complete the cut path.

Yet another cutting method utilizing the continuous cutting edge is referred to hereinabove as scoring of tissue. A sharp continuous edge may be used to score a tissue layer, i.e., to cut into the layer along a cutting path without cutting through it, by applying an amount of pressure that is insufficient to result in a cut completely through the tissue layer. Again, this amount of pressure will be carefully chosen by the skilled user of the instrument based on the sharpness of the blade, thickness of the tissue, and the relative resistance of the tissue layer to cutting. A tissue layer which has been scored along a chosen cutting path may be easily removed by pulling on the tissue to induce a tear in the tissue along the scored path. The scored tissue will tear clearly along that path. Of course, the scoring method may be performed using a relatively less sharp or a dull cutting edge, by applying relatively more pressure to the instrument, as needed.

The above-identified cutting methods also may be accomplished using a blade other than a blade having a continuous cutting edge. For example, where intermittent cutting is desired, the user may prefer to utilize a serrated cutting edge. Where a serrated edge is used, e.g., see FIGS. 7 and 8, varying the application and release of pressure to the instrument is unnecessary to accomplish discontinuous cutting. Instead, the discontinuous configuration of the blade cutting edge itself accomplishes the task. That is, the portions of the cutting edge that jut outward, i.e., the teeth, will meet the tissue layer first and, upon application and maintenance of pressure to the instrument, will cut through the tissue layer. The alternating recessed portions either will not contact the tissue or will contact it in such a manner so as to leave intermittent portions of the tissue uncut or scored. The serrated blade is guided by the surgeon along the cutting path of the tissue. During movement of the blade, a relatively invariant amount of pressure is applied to the instrument. Again, the choice of pressure is determined by the skilled user by taking into account a number of factors, as explained above.

It can be seen, then, that the capsulotomy knife of the invention can be controlled very accurately and easily so that its sharp edge is always directed along the desired cutting path. The simplicity and rugged nature of the knife mean that it can have a long life of useful service. The knife can be made with a blade mounting unit capable of handling interchangeable blades so as to prolong its useful life. Alternatively, a knife made of inexpensive materials can be considered disposable.

A knife according to the invention would be useful not only in ocular surgery but also in any kind of arthroscopic or laparoscopic procedure, e.g., in the knee, in the belly for cutting around the gall bladder, or in the brain. For this type of use, the main body of the knife and the moveable rod portion of the turning unit could be made of a flexible plastic. In addition, other surgical cutting instruments for use where precise but remote control is needed, could be fashioned in the same way.

Figure 6:
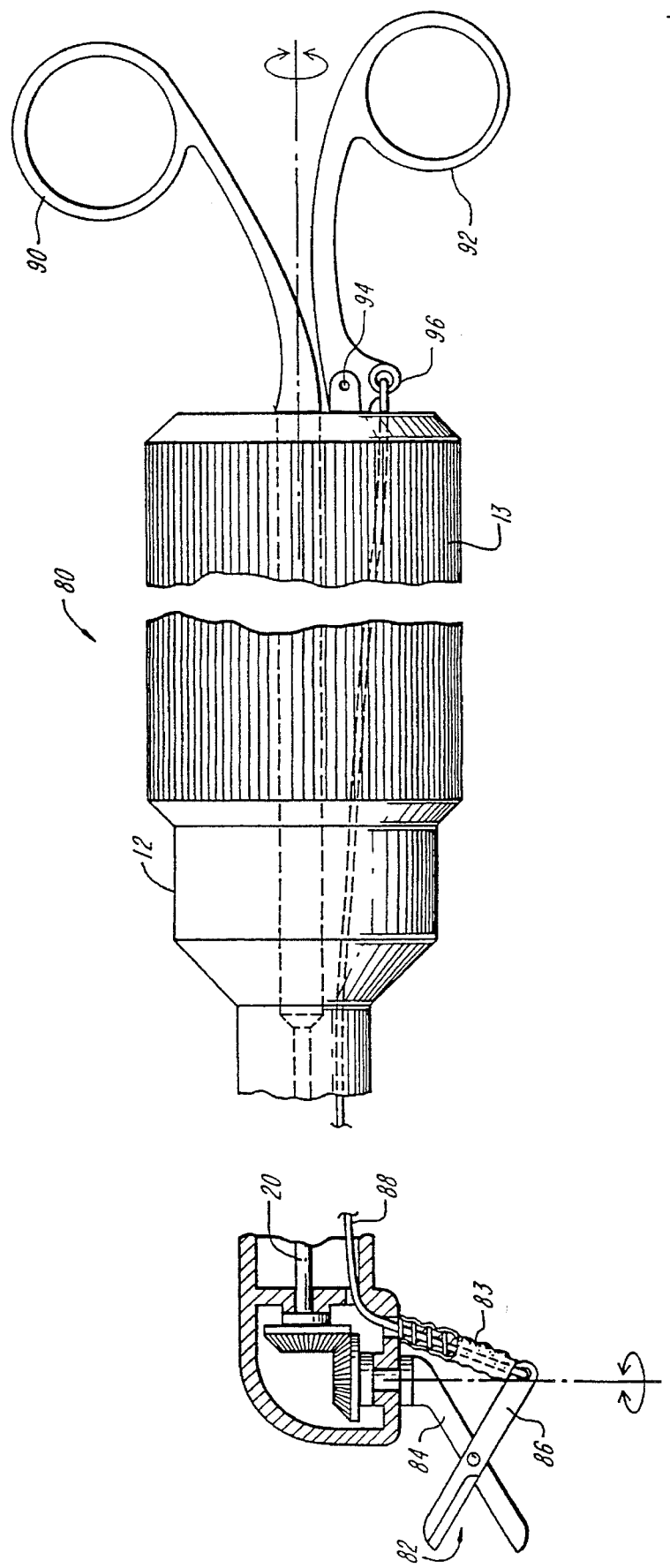
FIG. 6 is a side perspective view of an embodiment having micro surgical scissors according to the invention.

For example, as shown in FIG. 6, surgical scissors 80, with a rotatable travel path of more than 270° in either direction, have a tubular main body 12 through which extends turning unit 20 with a micro gear mechanism 30 similar to that for a capsulotomy knife turning mechanism. Micro scissors 82, which are spring loaded with a sheathed coiled spring 83 so as to remain in an open position until urged closed, are stiffly mounted by one scissors handle 84 to the short end of turning unit 20. A flexible wire 88, which is connected by a small ball joint pivot to unattached scissors handle 86, runs from the scissors handle back through the tubular instrument body 12, adjacent to the turning unit. Knurled barrel handle 13 closes off the open end of the long section of the instrument body, and supported at the end of the handle are opposed scissors loop handles 90 and 92. Loop 90 is stiffly connected to the turning unit and extends above a plane through its axis. Loop 92 is connected by pivot 94 to barrel handle 13 and extends below the turning unit plane. Flexible wire 88, extending from the lower scissors handle 86, is attached to lower loop 92 by a hinge 96.

To operate the scissors, the surgeon inserts the thumb of the dominant hand into loop 90 and the middle finger into loop 92. A twisting motion of the hand will cause the turning mechanism to rotate, as described before, and will result in positive controlled rotation of the micro scissors. In this manner, the scissors can be kept oriented along a desired cutting path. To provide the scissors cutting action, the surgeon applies pressure from the middle finger on loop 92 and squeezes the loop upwards, towards loop 90. This movement flexes hinge 94 and consequently applies a pulling action to wire 88. Action of the wire on scissors handle 86 then brings the cutting edges of the scissors into juxtaposition. As soon as the pressure on loop 92 is released, action of spring 83 forces scissors handles 84 and 86 apart and restores the scissors to their open configuration.

Other embodiments of the invention will be apparent to those skilled in the art from a consideration of this specification or practice of the invention disclosed herein. It is intended that the specification and the examples be considered as exemplary only, with the true scope and spirit of the invention being indicated by the following claims.

What is claimed is:

1. A surgical knife comprising:

a tubular main body having a primary axis, a first housing portion aligned along the primary axis, and a second housing portion disposed adjacent to the first housing portion;

a blade mount attached to the second housing portion and journaled for rotation about a secondary axis disposed at an angle with respect to the primary axis; and a blade having a cutting edge, the blade mounted to the blade mount to extend from the second housing portion of the tubular body along the secondary axis;

a turning unit disposed within the second housing portion in cooperation with the blade mount to rotate the blade mount; and a movement control element disposed to extend from the first housing portion of the main body and operatively connected to the turning unit to cause movement of the turning unit, wherein movement of the control element causes rotation of the blade about the secondary axis.

2. The surgical knife of claim 1, said cutting edge comprising a semi-circular shape.

3. The surgical knife of claim 1, said cutting edge being of a sharpness sufficient to cut into a tissue layer without cutting through said tissue layer.

4. The surgical knife of claim 1, said cutting edge being continuous.

5. The surgical knife of claim 1, said cutting edge being serrated.

6. A method of performing micro surgery on a tissue of the body, said method comprising the steps of providing the surgical knife of claim 5; and applying said serrated cutting edge to the tissue layer in a continuous manner upon movement of the cutting edge along a cutting path using an amount of pressure sufficient to achieve intermittent cuts through the tissue layer.

7. A method of performing micro surgery on a tissue of the body, said method comprising the steps of providing the surgical knife of claim 1; and applying the cutting edge of said knife to a tissue layer with pressure sufficient to cut through said tissue layer in a continuous manner upon movement of said edge along a cutting path.

8. A method of performing micro surgery on a tissue of the body, said method comprising the steps of (a) providing the surgical knife of claim 1;

(b) applying said cutting edge to a tissue layer sufficient to cut a discrete length of said tissue layer along a cutting path; and (c) releasing pressure on said cutting edge for a distance along said cutting path sufficient to leave a discrete length of said tissue layer along said cutting path uncut.

9. A method of performing micro surgery on a tissue of the body, said method comprising the steps of providing the surgical knife of claim 1 or 3; and applying the cutting edge of said knife to a tissue layer with pressure sufficient to cut into said tissue layer upon movement of said edge along a cutting path, but insufficient to cut through said tissue layer.

10. The method of claim 8, further comprising repeating steps (b) and (c).

11. The method of claim 7, 9, or 8, further comprising peeling off the cut portion of said tissue layer.

12. The method of claim 7, 9, 6, or 8, further comprising:
rotating said blade by manual manipulation of the movement control element to direct the orientation of said blade with respect to said knife;
manually orienting said knife while simultaneously rotating said blade to form a non-linear incision in said tissue layer; and
manually removing said cutting edge from cutting contact with said tissue layer.

13. The surgical knife of claim 1, wherein
said second housing portion is disposed at an angle with respect to said first housing portion.

14. The surgical knife of claim 13, wherein said angle between said first and second housing portions of said tubular body is between 80° and 110°.

15. The surgical knife of claim 13 wherein said turning unit comprises a micro gear.

16. The surgical knife of claim 1, wherein said turning unit comprises a linear rotatable element disposed through the first and second housing portions of said main body.

17. The surgical knife of claim 1, wherein
the turning unit comprises first and second transversely oriented bevel gears.

18. The surgical knife of claim 1, wherein said second housing portion of said main body and said turning unit comprise flexible portions.

19. The surgical knife of claim 1, wherein the cutting edge of the blade is arcuate.

20. The surgical knife of claim 1, wherein the blade is triangular.

21. The surgical knife of claim 1, wherein the movement control element comprises a knob mounted to an end of the turning unit for rotation about the primary axis.

22. The surgical knife of claim 1, wherein the movement control element comprises a slide control knob.

23. The surgical knife of claim 1, wherein the movement control element comprises a knob mounted to the turning unit for rotation about an axis perpendicular to the primary axis.

24. A surgical knife comprising:
a tubular main body having a primary axis extending from one end to another end of the tubular main body, a blade mount disposed to extend from the tubular main body near the one end, and a movement control element disposed to extend from the tubular main body and spaced from the blade mount a distance along the primary axis toward the other end;
a turning unit disposed within the tubular main body, the turning unit comprising a band aligned along the primary axis within the main body and extending from the movement control element to the blade mount and cooperative with the blade mount and the movement control element; and
a blade having a cutting edge, the blade being mounted to the blade mount to extend at an angle to said primary axis, whereby the orientation of the blade with respect to the main body may be altered by movement of the movement control element.

25. The surgical knife of claim 24, wherein the movement control element comprises a knob.

26. The surgical knife of claim 25 wherein said blade is detachably mounted on said blade mount.

27. The surgical knife of claim 24, said band being wrapped around said blade mount near the one end of said main body and wrapped around said knob near the other end of said main body.

28. The surgical knife of claim 27 wherein said band is selected from a group consisting of a coiled spring, silicone rubber, polytetrafluoroethylene, and polyurethane elastomer.

29. A surgical knife comprising:
a tubular main body having a primary axis extending from one end to another end of the tubular main body, a blade mount disposed to extend from the tubular main body near the one end, and a slide control element disposed to extend from the tubular main body and spaced from the blade mount a distance along the primary axis toward the other end;
a turning unit disposed within the tubular main body, the turning unit comprising rack and pinion elements cooperative with the blade mount and the slide control element; and
a blade having a cutting edge, the blade being mounted to the blade mount to extend at an angle to the primary axis, whereby the orientation of the blade with respect to the main body may be altered by movement of the slide control element.

30. A remotely operable surgical knife comprising:
a tubular main body having a primary axis, said tubular main body comprising an elongated first portion aligned along said primary axis and a shorter second portion extending from said first portion to form an angle with respect to said first portion;
a turning unit disposed within said main body, said turning unit comprising:
a turning mechanism comprising a micro gear in the main body at the juncture of the first and second portions, the micro gear comprising rack and pinion elements;
a movable element extending through the first portion of said main body and attached to the turning mechanism, the movable element having an end attached to a slide control knob, wherein movement of the slide control knob in the direction of the micro gear causes the rotation of the blade; and
a blade mounting portion in the second portion of the main body and attached to said turning mechanism; and
a blade mounted on said blade mounting portion of said turning unit,
wherein the orientation of a cutting edge of said blade with respect to said main body is determined by movement of said movable element.

31. Remotely operable surgical scissors comprising:
a tubular main body comprising an elongated first portion having one end and a shorter second portion having one end, said second portion extending from said first portion distal to the one end of said first portion to form an angle greater that 45° to said first portion;
a turning unit extending through said main body, said turning unit comprising
a turning mechanism in the main body at the junction of the first and second portions, said turning mechanism comprising a micro gear,
a movable element through the first portion of said main body and having one end attached to the turning mechanism, and
a scissors mounting portion in the second portion of the main body;
scissors mounted on said scissors mounting portion, wherein movement of a second end of said moveable element causes rotation of said scissors about an axis generally aligned with the second portion of the main body; and a scissors controlling element connected to said scissors and extending through said main body from said one end of said second portion to said one end of said first portion for controlling operation of said scissors.

32. A method of performing eye surgery within an interocular incision in the sclera and conjunctiva, between the cornea and an anterior capsular membrane, and through an iris, for incising a portion of said anterior capsular membrane, said method comprising:

manually inserting an ophthalmic knife through said interocular incision, said ophthalmic knife comprising:
- a tubular main body having a primary axis, a first housing portion aligned along the primary axis, and a second housing portion disposed adjacent to said first housing portion;
- a blade mount attached to the second housing portion and journaled for rotation about a secondary axis disposed at an angle with respect to the primary axis; and
- a blade having a cutting edge, the blade mounted to the blade mount to extend from the second housing portion of the tubular body along the secondary axis;
- a turning unit disposed within the second housing portion in cooperation with the blade mount to rotate the blade mount; and
- a movement control element disposed to extend from the first housing portion of the main body and operatively connected to the turning unit to cause movement of the turning unit, wherein movement of the control element causes rotation of the blade about the secondary axis;

manually rotating said blade by manual manipulation of said movement control element to direct the orientation of said blade with respect to said ophthalmic knife;

manually orienting said ophthalmic knife while simultaneously rotating said blade to form a continuous, non-linear incision in said anterior capsular membrane; and manually removing said ophthalmic knife from said incision.

* * * * *